United States Patent
Charles et al.

(10) Patent No.: US 9,844,314 B2
(45) Date of Patent: Dec. 19, 2017

(54) INCREASED DEPTH OF FIELD MICROSCOPE AND ASSOCIATED DEVICES, SYSTEMS, AND METHODS

(71) Applicant: NOVARTIS AG, Basel (CH)

(72) Inventors: Steven T. Charles, Memphis, TN (US); Michael Papac, North Tustin, CA (US)

(73) Assignee: Novartis AG (CH)

(*) Notice: Subject to any disclaimer, the term of this patent is extended or adjusted under 35 U.S.C. 154(b) by 43 days.

(21) Appl. No.: 14/444,437

(22) Filed: Jul. 28, 2014

(65) Prior Publication Data

US 2016/0022133 A1    Jan. 28, 2016

(51) Int. Cl.

| A61B 3/00 | (2006.01) |
|---|---|
| A61B 3/13 | (2006.01) |
| A61B 90/20 | (2016.01) |
| G02B 21/22 | (2006.01) |
| G02B 21/24 | (2006.01) |
| G02B 27/00 | (2006.01) |

(52) U.S. Cl.
CPC .............. *A61B 3/0025* (2013.01); *A61B 3/13* (2013.01); *A61B 90/20* (2016.02); *G02B 21/241* (2013.01); *G02B 27/0075* (2013.01); *G02B 21/22* (2013.01)

(58) Field of Classification Search
CPC ......... A61B 3/0025; A61B 3/13; A61B 3/132; A61B 3/14; A61B 19/5212; A61B 19/5223; A61B 19/5225; G02B 27/2285; A61F 9/007
USPC .......... 351/206, 211; 600/558; 359/362-363, 359/368-369, 372-380, 382-383, 432, 359/197.1, 209.1, 210.1; 250/201.1-201.4
See application file for complete search history.

(56) References Cited

U.S. PATENT DOCUMENTS

| 6,075,585 A | 6/2000 | Minne et al. |
|---|---|---|
| 6,552,878 B2 | 4/2003 | Sato et al. |
| 8,025,403 B2 | 9/2011 | Maloca et al. |
| 2004/0264765 A1* | 12/2004 | Ohba ..................... G02B 21/22 382/154 |
| 2007/0057211 A1* | 3/2007 | Bahlman ............ G01N 21/6452 250/584 |
| 2007/0279733 A1 | 12/2007 | Sander |
| 2013/0128223 A1* | 5/2013 | Wood ....................... A61B 3/14 351/206 |

(Continued)

FOREIGN PATENT DOCUMENTS

WO    2009140086 A2    11/2009

*Primary Examiner* — Thomas K Pham
*Assistant Examiner* — Ibrahima Diedhiou
(74) *Attorney, Agent, or Firm* — Keiko Ichiye

(57) ABSTRACT

An ophthalmic surgical microscope can include a movable optical element positioned in an optical pathway of light reflected from a surgical field. The movable optical element can be configured to oscillate in a direction along the optical pathway. The microscope can include an actuator coupled to the movable optical element and configured to move in response to a control signal. The microscope can include a computing device in communication with the actuator and configured to generate the control signal to move the movable optical element. In some embodiments, the computing device is configured to generate the control signal to move the movable optical element with an oscillation frequency greater than the critical flicker fusion rate.

15 Claims, 5 Drawing Sheets

(56) References Cited

U.S. PATENT DOCUMENTS

| | | | |
|---|---|---|---|
| 2013/0158584 A1* | 6/2013 | Underwood | A61F 9/00763 606/171 |
| 2013/0229625 A1 | 9/2013 | Wei et al. | |
| 2014/0005555 A1 | 1/2014 | Tesar | |

* cited by examiner

INCREASED DEPTH OF FIELD MICROSCOPE AND ASSOCIATED DEVICES, SYSTEMS, AND METHODS

BACKGROUND

Technical Field

Embodiments disclosed herein are related to ophthalmic surgical microscopes. More specifically, embodiments described herein relate to an increased depth of field microscope including a movable optical element.

Related Art

Doctors can use surgical microscopes during ophthalmic surgical procedures to see fine details of a patient's eye. A successful procedure can depend on the doctor's ability to view the patient's eye clearly using the microscope. One measure of the doctor's ability to view the patient's eye is the depth of field of the microscope. The depth of field can describe an extent of a microscope subject perceivable by an observer to be in focus at the same time along a direction of the optical pathway of light reflected from the subject. For example, the depth of field can describe the longitudinal extent of a patient's eye that is in focus at the same time for a doctor along the longitudinal axis or z-axis of the microscope. A larger depth of field provides better spatial awareness to the doctor during a surgical procedure because more of the patient's eye is in focus at the same time.

Some conventional methods for increasing depth of field include implementing a larger objective lens in the microscope. Large objective lenses, however, can be costly and add unwanted bulk to the microscope. Diaphragm apertures can also be implemented, which allow for the microscope to have a smaller aperture to increase the depth of field. However, a smaller aperture reduces the photon flux or amount of light passing through the microscope optics. Conventional methods for increasing depth of field have thus been unsatisfactory.

The critical flicker fusion (CFF) rate is a quantity in psychophysics describing the frequency beyond which flicker or individual images in a successive image set are no longer independently perceivable by an observer. Above the CFF rate, the observer's brain integrates or fuses the individual images into a single image. The CFF rate has been utilized in display technology for line sequential stereo, field sequential stereo, line sequential color, field sequential color, etc. For example, in a field sequential color system, an entirely red frame, an entirely green frame, and an entirely blue frame are successively provided to the observer above the CFF rate. The observer's brain fuses the single-color frames so that the observer perceives a color image as opposed to the individual frames. Conventional microscopes do not utilize the CFF rate.

SUMMARY

The presented solution fills an unmet medical need with a unique solution to provide an ophthalmic surgical microscope with a moving optical element that oscillates at a frequency greater than the critical flicker fusion rate such that an observer perceives a volumetric image of the surgical field. The increased depth of field as a result of the moving optical element can improve the doctor's view of the surgical field.

Consistent with some embodiments, an ophthalmic surgical microscope can include: a movable optical element positioned in an optical pathway of light reflected from a surgical field, the movable optical element being configured to oscillate in a direction along the optical pathway; an actuator coupled to the movable optical element and configured to move in response to a control signal; and a computing device in communication with the actuator and configured to generate the control signal to move the movable optical element.

Consistent with some embodiments, a method of operating an ophthalmic surgical microscope can include: controlling a movable optical element positioned in an optical pathway of light reflected from a surgical field to oscillate in a direction along the optical pathway; receiving the light reflected from the surgical field at an image sensor; generating image data based on the light received at the image sensor, the image data being representative of a plurality of focal planes perpendicular to the optical pathway and generated by oscillation of the movable optical element; processing the image data; and providing the processed image data to a display device.

Consistent with some embodiments, an ophthalmic surgical microscope can include: an optical element positioned in an optical pathway of light reflected from a surgical field, the optical element being controllable to generate an oscillating focal plane perpendicular to the optical pathway; an actuator coupled to the optical element and configured to move the oscillating focal plane in response to a control signal; and a computing device in communication with the actuator and configured to generate the control signal to move the oscillating focal plane.

Additional aspects, features, and advantages of the present disclosure will become apparent from the following detailed description.

Figure 1:
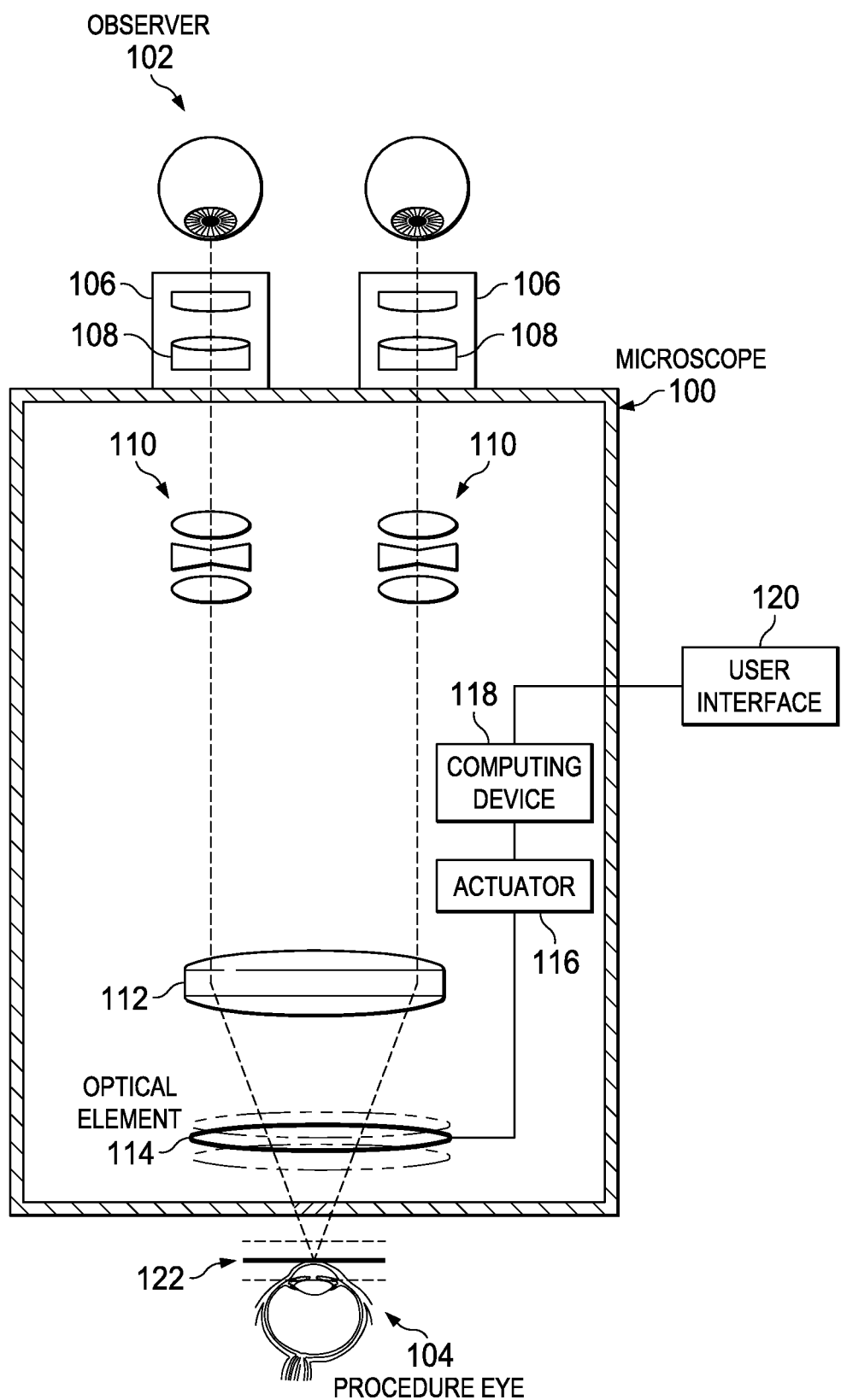
FIG. 1 is a diagram illustrating an ophthalmic surgical microscope.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The present disclosure describes an ophthalmic surgical microscope with a movable optical element. The movable optical element can oscillate along a direction of the optical pathway of light reflected from the surgical field at a frequency greater than the CFF rate. Oscillation of the movable optical element can provide an increased depth of field for the microscope. An observer of the surgical field using the microscope optics can perceive a volumetric image. In some embodiments, an image sensor/camera can be implemented in the microscope. Image data generated by the image sensor/camera can be processed to enhance the image by selecting and overlaying in-focus portions of the image data. The enhanced image can be provided to a display device.

The devices, systems, and methods of the present disclosure provide numerous advantages, including: (1) improving efficacy of surgical procedures by providing greater spatial awareness for the doctor; (2) improving microscope optics by providing increased depth of field; and (3) avoiding costs associated with implementing conventional techniques to provide increased depth of field; and (4) increasing usability for surgical microscopes by maximizing surgical field sight for all doctors.

Figure 2:
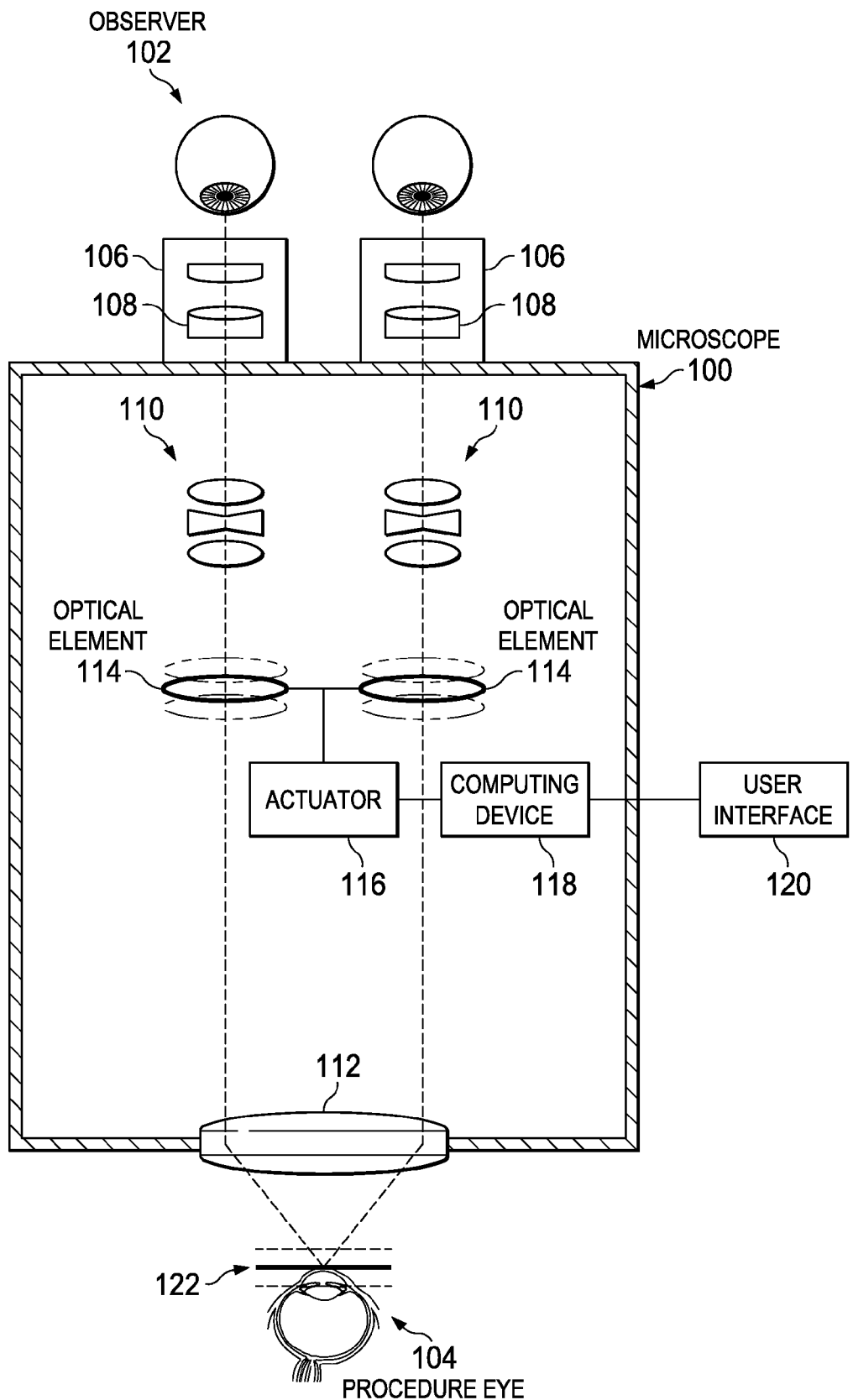
FIG. 2 is a diagram illustrating an ophthalmic surgical microscope.

FIGS. 1 and 2 illustrate an ophthalmic surgical microscope 100. An observer 102 can view the surgical field, such as a procedure eye 104, using the microscope 100. The observer 102 can be a healthcare professional, such as a doctor or surgeon performing a diagnostic, surgical, and/or other medical procedure. The procedure eye 104 can be that of a patient undergoing the medical procedure.

One or more lenses, mirrors, filters, gratings, and/or other optical components can comprise an optical train of the microscope 100. The optical components can be positioned in the optical pathway of light reflected from the surgical field. For example, eyepieces 106 can include optical components 108, and the body of the microscope 100 can include optical components 110 and objective lens 112. The optical components 108 and 110, and objective lens 112 are exemplary, and in various embodiments, the microscope 100 can include more or fewer lenses and/or other optical components to focus the light and/or magnify the image.

One or more components of the microscope 100 can be utilized to provide coarse and/or fine focus of the microscope optics for the observer 102. Course focus can be, for example, motor/gear driven and volitionally controlled by a surgeon using, for example, 7 a foot pedal. Course focus controls can generally provide relatively slower and larger amplitude focus changes. Fine focus can be, for example, automatically driven by servomotors and/or other suitable actuators. Fine focus controls can generally provide relatively faster and smaller amplitude focus changes.

The surgical microscope 100 can include an optical element 114. The optical element 114 can be a component of the fine focus controls of the microscope 100. The optical element 114 can be an optical lens, mirror, etc. For example, the optical element 114 can be an optical lens with low magnification power. The optical element 114 can be positioned in the optical pathway of light reflected from the surgical field. In some embodiments, the optical element 114 is disposed within the microscope 100. The optical element 114 can be variously positioned in the optical train of the microscope 100 in different embodiments. For example, the optical element 114 can be positioned between the optical components 108 and the optical components 110, between the optical components 110 and the objective lens 112, between the objective lens 112 and the surgical field, between the observer 102 and the objective lens 112, etc. The microscope 100 can include one or more movable optical elements 114 depending on, e.g., where in the optical pathway and/or the optical train of the microscope 100 the movable optical elements 114 are positioned. For example, as shown in FIG. 1, one optical element 114 is positioned between the objective lens 112 and surgical field. For example, as shown in FIG. 2, the microscope 100 includes two movable optical elements 114. The movable optical elements 114 can be positioned in separate optical pathways respectively associated with each eye of the observer 102 (e.g., in a stereo microscope).

In some embodiments, the optical element 114 is disposed outside of the microscope 100, e.g., as a separate component. The optical element 114 can be part of a component configured to operate in contact with the procedure eye 104, as a contact lens, or spaced from the procedure eye 104, as a non-contact lens. For example, the optical element 114 can be included as one component of a lens-patient interface positioned below the objective lens 112 of the microscope 100, e.g., between the objective lens 112 and the procedure eye 104. For example, the optical element 114 can be integrated, e.g., along with other optical components, into a common component or optical block, such as a hand-held device, a lens holder, an adapter, or other component. The optical element 114, the lens-patient interface, and/or the optical block can be operated with or without a defined optical/optomechanical relationship to the microscope 100. In some embodiments, the optical element 114, the lens-patient interface, and/or the optical block can be coupled to the microscope 100, directly or indirectly, such that the optical element 114, the lens-patient interface, and/or the optical block have a defined optical/optomechanical relationship to the microscope. For example, direct or indirect coupling between the optical element 114, the lens-patient interface, and/or the optical block, and the microscope 100 can include one or more of a suspension system, a mechanical frame, a protruding arm, a conical structure, a magnetic member, an elastic member, and a plastic member.

The optical element 114 can be a movable optical element. The movable optical element 114 can be configured to oscillate in a direction along the optical pathway of the light reflected from the surgical field. For example, the optical element 114 can oscillate along the direction of the longitudinal axis or z-axis of the microscope 100. The displacement of the optical element 114 during oscillation can be, for example, between approximately 50 microns and approximately 500 microns, between approximately 100 microns and approximately 400 microns, between approximately 200 microns and approximately 300 microns, and between approximately 100 microns and approximately 200 microns, among others, including values such as approximately 200 microns, approximately 250 microns, approximately 300 microns, etc., though larger and smaller displacements are contemplated. Positions of the optical element 114 during oscillation are shown in phantom lines in FIGS. 1-4. (The displacement of the optical element 114 is exaggerated for improved understanding.) The optical element 114 can move with an oscillation frequency greater than the critical flicker fusion (CFF) rate. An oscillation frequency greater than 70 Hz can be understood to exceed the CFF rate. In various embodiments, the optical element 114 can move with an oscillation frequency between approximately 50 Hz and approximately 100 Hz, between approximately 60 Hz and approximately 90 Hz, between approximately 60 Hz and approximately 80 Hz, above approximately 60 Hz, above approximately 70 Hz, etc., though higher and lower frequencies are contemplated. In some embodiments, the optical element 114 can move with a user-specified oscillation frequency in response to a user input received at a user interface 120, described in greater detail below.

The optical train of the microscope 100 can have a focal plane 122. The focal plane 122 is perpendicular to the optical pathway of the light reflected from the surgical field. Oscillation of the optical element 114 can generate a plurality of focal planes 122 at varying distances. The focal plane 122 can thus be described as oscillating. The displacement of the focal plane 122 in the direction along the optical pathway can be, for example, between approximately 50 microns and approximately 500 microns, between approximately 100 microns and approximately 400 microns, between approximately 200 microns and approximately 300 microns, and between approximately 100 microns and approximately 200 microns, among others, including values such as approximately 200 microns, approximately 250 microns, approximately 300 microns, etc., though larger and smaller displacements are contemplated. The focal planes 122 generated by oscillation of the optical element 114 are shown in phantom lines in FIGS. 1-4. (The distance between the optical planes 122 is exaggerated for improved understanding.) Different portions of the surgical field can be in focus and out of focus in the various focal planes 122. The microscope 100 presents views of the surgical field in the focal planes 122 as a collection or stack of images in the direction along, e.g., the z-axis of the microscope 100 to the observer 102. When the optical element 114 is oscillated at an oscillation frequency higher than the CFF rate, the brain of the observer 102 can integrate the views of the focal planes 122. Thus, the observer 102 can perceive the surgical field as a volumetric image (rather than as individual images).

The microscope 100 can include an actuator 116. The actuator 116 can be coupled to the one or more movable optical elements 114 such that the actuator 116 causes movement of the movable optical element 114. In some embodiments, the actuator 116 can move and cause corresponding movement of the movable optical element 114. In some embodiments, one actuator 116 is coupled to each movable optical element 114. In some embodiments, one actuator 116 is coupled to more than one movable optical element 114. The actuator 116 can be a voice coil, a non-commutated actuator such as a moving magnet actuator, a piezoelectric actuator, or other suitable actuators. For example, the actuator 116 can be an annular moving magnet, such a neodymium iron boron ring magnet. For example, the actuator 116 can be a moving magnet linear motor. The actuator 116 can be configured to move the movable optical element in response to a control signal received from a computing device 118.

In some embodiments, the optical element 114 does not move. Similarly, in some embodiments, the actuator 116 does not move. For example, the optical element 114 can be a liquid lens, and the actuator 116 can be a voltage source. A control signal generated by the computing device 118 and provided to the actuator 116 can be a voltage command. The liquid lens can utilize the electrowetting principles. The voltage applied to the liquid lens can change its focal length, and correspondingly the position of the focal plane 122. By varying the voltage applied to the liquid lens, the focal plane 122 can be oscillated without corresponding movement of the optical element 114 and/or the actuator 116. A plurality of focal planes 122 can be generated at varying distances as described herein. Thus, the optical element 114 can be controllable to generate an oscillating focal plane 122 perpendicular to the optical pathway of light reflected from the surgical field. The actuator 116 can be coupled to the optical element 114 and configured to move the oscillating focal plane 122 in response to a control signal. The computing device 118 can be in communication with the actuator 116 and configured to generate the control signal to move the oscillating focal plane 122. The liquid lens can also be implemented in the microscope 110 for optical image stabilization.

The computing device 118 can be in communication with the actuator 116 and configured to generate a control signal to move the movable optical element 114. For example, the computing device 118 can generate the control signal to cause the actuator 116 to move the optical element 114 at an oscillation frequency greater than the CFF rate. The computing device 118 can include any suitable processor, memory, or processing circuit for generating the control signal, receiving user input from the user interface 120, receiving and processing image data from an image sensor/camera 124, providing processed image data to a display device 126, and other steps described herein or necessary to accomplish the steps described herein. In some embodiments, the computing device 118 is part of the microscope 100. In some embodiments, the computing device 118 is a separate component that is not part of the microscope 100 itself and is rather in communication with the actuator 116 and the microscope 100.

The computing device 118 can be in communication with a user interface 104. In some embodiments, the user interface 104 can be a user-facing component of the computing device 118 such that the user interface 104 is a part of the microscope 100. In some embodiments, the user interface 104 is a separate component that is not part of the microscope 100 itself and is rather in communication with the computing device 118 and the microscope 100. The user interface 104 can include input devices or systems, including by way of non-limiting example, a keyboard, a mouse, a joystick, dials, and buttons, among other input devices. The user interface 104 can be a display (including, for example, a touchscreen display) configured to present images or other data (e.g., microscope settings, display settings, etc.) to a user, such as images of surgical field during the surgical procedure. An observer 102 can provide a user-specified oscillation frequency for the optical element 114 via the user interface 104. For example, the observer 102 can be provide a user-specified oscillation frequency to fine tune movement of the optical element 114 such that the observer 102 perceives a volumetric image when viewing the surgical field.

Figure 3:
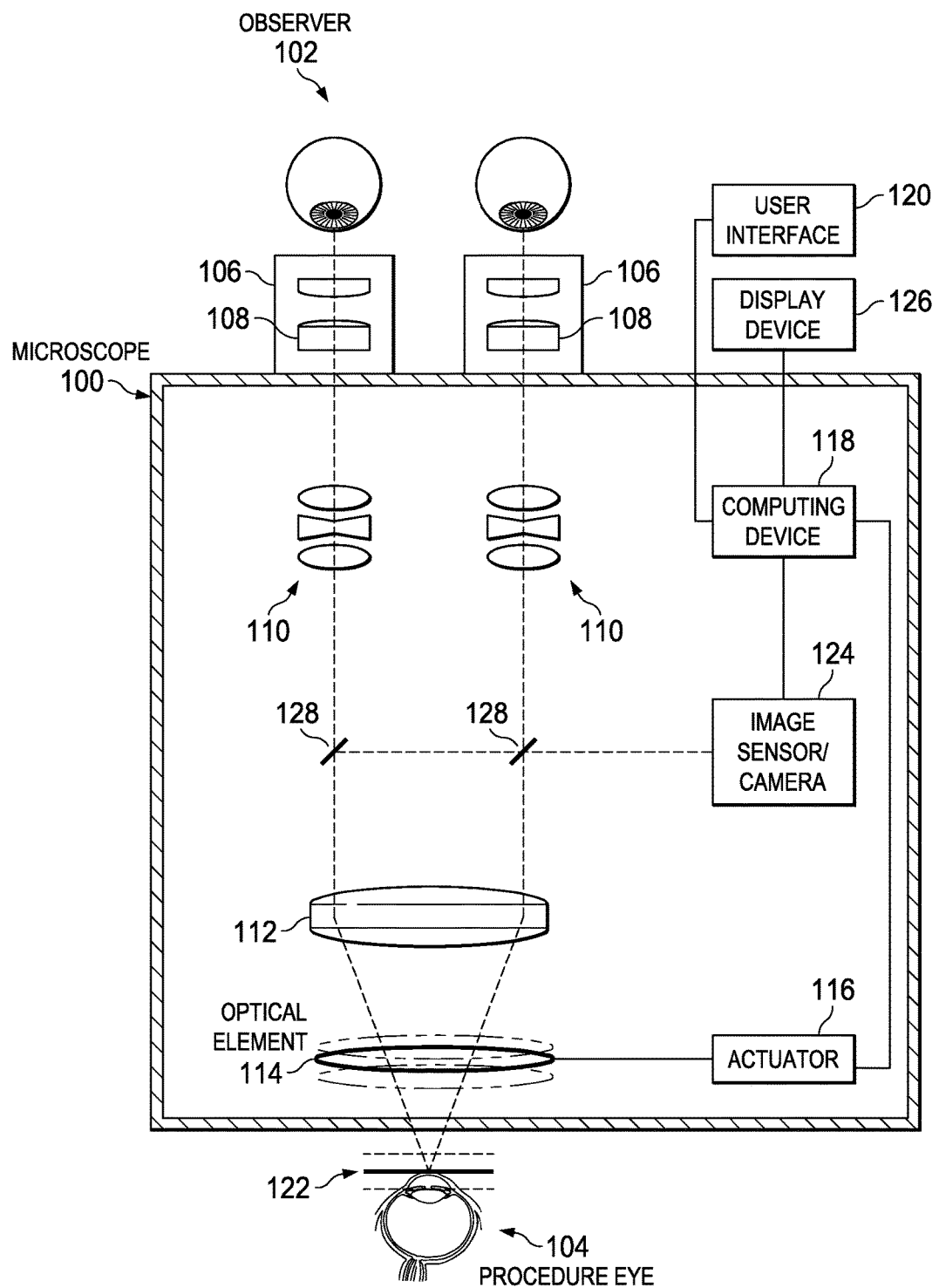
FIG. 3 is a diagram illustrating an ophthalmic surgical microscope including an image sensor/camera.
Figure 4:
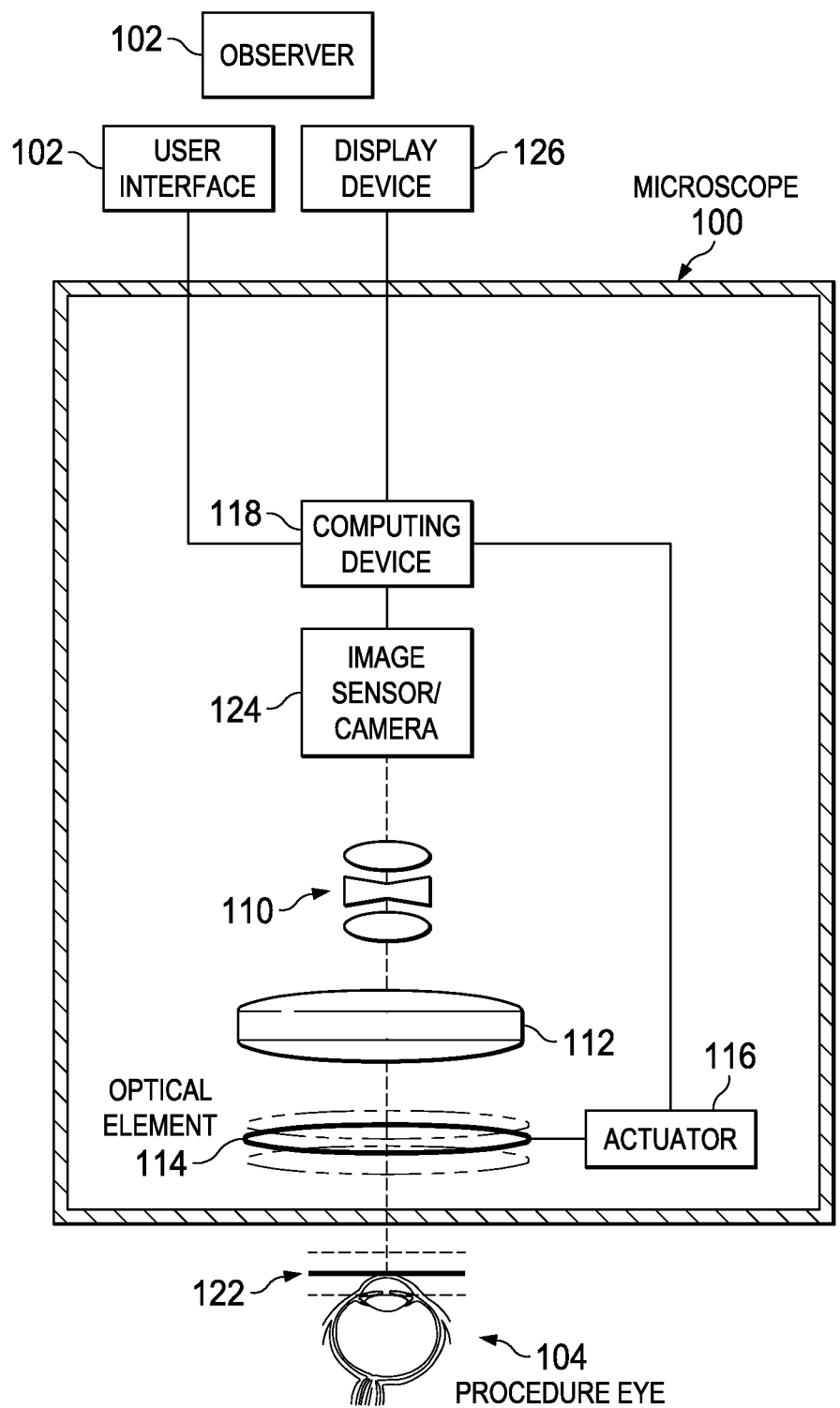
FIG. 4 is a diagram illustrating a digital microscope.

FIG. 3 illustrates the ophthalmic surgical microscope 100 including an image sensor/camera 124. FIG. 4 illustrates a digital microscope 100. The microscope 100 of FIGS. 3 and 4 can be similar to the microscope 100 of FIGS. 1 and 2, such as by including the movable optical element 114, the actuator 116, and the computing device 118. Further, the microscope 100 of FIG. 3 can be similar to the microscope 100 of FIGS. 1 and 2, such as by including microscope optics for the observer 102 to view the surgical field through the microscope 100. FIG. 4 omits the microscope optics for the observer 102 to view the surgical field directly through the microscope 100. The microscope 100 of FIGS. 3 and 4 include a display device 126 to display images of the surgical field captured by the image sensor/camera 124.

The image sensor/camera 124 can be positioned in the optical pathway of the light reflected from the surgical field. For example, the optical element 114 can be disposed in the optical pathway between the surgical field and the image sensor/camera 124. The microscope 100 can include one or more beam splitters 128 to direct at least a portion of the light to the imaging sensor/camera 124. The image sensor/camera 124 can include a charge-coupled device (CCD) sensor, a complementary metal-oxide-semiconductor (CMOS) sensor, or other suitable image sensor. The image sensor/camera 124 can be configured to receive light reflected from the surgical field. The image sensor/camera 124 can include circuitry to generate electrical data and/or image data from the received light. The image sensor/camera 124 can be in communication with the computing device 118. The image sensor/camera 124 can provide the image data to the computing device 118. In some embodiments, the computing device 118 generates the image data when electrical data is received from the image sensor/camera 124. The computing device 118 can process the image data and provide the processed image data to the display device 126.

The display device 126 can be in communication with the computing device 118. The display device 126 can display images of the surgical field captured by the image sensor/camera 124, including the processed image data received from the computing device 118. In some embodiments, the display device 126 is part of the microscope 100. For example, the display device 126 can be a monitor disposed on or coupled to the microscope 100 to allow viewing by the observer 102 and/or other observers. In some embodiments, the display device 126 can be a separate component that is not part of the microscope 100 itself, and rather is in communication with the computing device 118 and the microscope 100. In various embodiments, the display device 126 can be a liquid crystal display (LCD), a light emitting diode liquid crystal display (LED-LCD), a digital micromirror device (DMD), heads up display, near to eye display, and/or other suitable display device. For example, the display device 126 can include transmissive elements (e.g., a backlit LED-LCD) or front-illuminated reflective elements.

Figure 5:
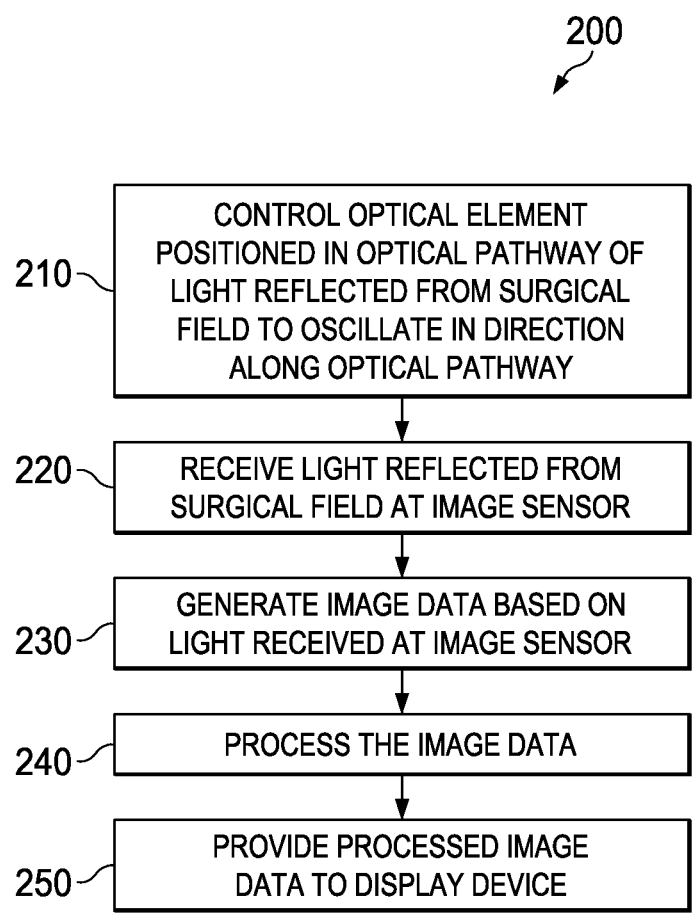
FIG. 5 is a flow diagram illustrating a method of operating an ophthalmic surgical microscope.

FIG. 5 provides a flow diagram of a method 200 of operating an ophthalmic surgical microscope. The method 100 can be further understood with reference to FIGS. 3 and 4. The method 200 can include, at step 210, controlling a movable optical element positioned in an optical pathway of light reflected from a surgical field to oscillate in a direction along the optical pathway. For example, the optical element 114 can be controlled to oscillate in a direction, e.g., along the longitudinal axis or z-axis of the microscope 100. In some embodiments, the optical element 114 can oscillate at a frequency greater than the CCF rate. In some embodiments, the optical element 114 can oscillate with a displacement in the direction along the optical pathway, for example, between approximately 200 microns and approximately 300 microns. In some embodiments, the computing device 118 can provide a control signal to the actuator 116 (e.g., a voice coil, a moving magnet actuator, and a piezoelectric actuator, etc.) coupled to the optical element 114 to move the movable optical element 114.

The method 200 can include, at step 220, receiving light reflected from a surgical field at an image sensor. For example, the light can be received at the image sensor/camera 124. The method 200 can include, at step 230, generating image data based on the light received at the image sensor. The image data can be representative of a plurality of focal planes 122 perpendicular to the optical pathway and generated by oscillation of the movable optical element 114. The image data can be generated by the image sensor/camera 124 and/or the computing device 118.

The method 200 can include, at step 240, processing the image data. Processing the image data can include any one or more signal processing steps to prepare the image data for display via the display device 126. For example, processing the image data can include noise reduction, filtering, sharpening, contrast manipulation, etc.

In some embodiments, processing the image data can include image enhancement by selecting in-focus image data associated with the plurality of focal planes. For example, imaging processing coupled with z-axis position sensing can be implemented to suppress out-of-focus image planes. As described above, portions of the image in each of the focal planes 122 generated by oscillation of the optical element 114 can include an in-focus portion and out-of-focus portion. At step 240, the in-focus portions can be selected and overlaid to generate processed, enhanced image data. In some embodiments, the in-focus image data is selected by first associating the image data with positions (e.g., displacement) of the optical element 114 during oscillation. For example, a laser interferometer, the Hall effect sensor, or other suitable principles/encoding schemes can be used to sense/track, e.g., the z-axis position of the movable optical element 114. The location of the focal planes 122 can be determined based on the position of the movable optical element 114. Further, the in-focus and out-of-focus focus portions of the image data can be determined based on the location of the focal planes 122. The in-focus portions of the image data can thus be selected based on the position of the movable optical element 114. In some embodiments, one or more electronic components can be used to select the image data with high frequency content. High frequency content can be associated with in-focus images, while out-of-focus or blurry images can be associated with low frequency content. A high pass filter and/or other electronic components, for example, can be used to filter high frequency content. Other suitable techniques to select in-focus portions of the image data can be implemented. In various embodiments, processing the image data can include other selection of particular image data (e.g., other than selection of in-focus image data) associated with the plurality of image planes 122.

The method 200 can include, at step 250, can include providing the processed image data to a display device. For example, the processed image can be provided to the display device 126.

The microscope 100 discussed herein can be a monocular or binocular microscope. It is understood that the microscope 100 can include one eyepiece for each eye of one or more observers 102 (e.g., two eyepieces each for a surgeon and an assistant). The teaching of the present disclosure can be implemented such that a volumetric image is perceivable through one or more eyepieces. The microscope 100 can be a compound, stereo, or digital microscope. The teaching of the present disclosure can be implemented in one or more optical paths of the microscope 100. For example, one optical element 114 can be implemented in the single optical pathway between the observer 102 and the surgical field in a compound or digital microscope. For example, one optical element 114 can be implemented in each of the two optical paths between the observer 102 and surgical field in a stereo microscope. In some embodiments, the optical element 114 can be oscillated for each eye of the observer 202. In some embodiments, the separate volumetric image sets are combined before being provided to eyes of the observer 102. In some embodiments, a volumetric image set is separately generated for each of multiple observers 102 (e.g., for one eye of each observer, for both eyes of each observer, separately for each eye of each observer, etc.).

Embodiments as described herein can provide devices, systems, and methods that provide an increased depth of field microscope with a movable optical element that oscillates at a frequency greater than the critical flicker fusion rate. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic surgical microscope, comprising:
   an objective lens;
   an optical element comprising an optical lens, the optical element positioned in an optical pathway of light reflected from a surgical field towards the objective lens, the optical element being controllable to generate an oscillating focal plane perpendicular to the optical pathway;
   an actuator coupled to the optical element and that moves the optical element separately from the objective lens to move the oscillating focal plane in response to a control signal;
   a computing device in communication with the actuator and that generates the control signal to move the oscillating focal plane;
   a position sensor that senses an z-axis position of the optical element;
   an image sensor positioned in the optical pathway and that receives the light reflected from the surgical field;
   the computing device that processes image data generated from the received reflected light by:
      selecting in-focus image data from the image data based on the sensed z-axis position of the optical element; and
      providing the in-focus image data for display.

2. The ophthalmic surgical microscope of claim 1, wherein:
   the computing device generates the control signal to move the focal plane with an oscillation frequency greater than the critical flicker fusion rate.

3. The ophthalmic surgical microscope of claim 1, wherein:
   the computing device generates the control signal to move the focal plane with an oscillation frequency greater than approximately 70 Hz.

4. The ophthalmic surgical microscope of claim 1, wherein:
   the optical element oscillates the focal plane in the direction along the optical pathway to generate a plurality of focal planes perpendicular to the optical pathway and perceivable by an observer as a volumetric image.

5. The ophthalmic surgical microscope of claim 1, wherein:
   the computing device generates the control signal to move the focal plane in the direction along the optical pathway between approximately 200 microns and approximately 300 microns.

6. The ophthalmic surgical microscope of claim 1, wherein:
   the actuator comprises at least one of a voice coil, a moving magnet actuator, a piezoelectric actuator.

7. The ophthalmic surgical microscope of claim 1, further comprising:
   a further optical element positioned in a further optical pathway of light reflected from the surgical field, the further optical element being controllable to generate a further oscillating focal plane perpendicular to the further optical pathway,
   wherein the optical element and the further optical element are positioned in optical pathways respectively associated with each eye of an observer.

8. The ophthalmic surgical microscope of claim 1, the computing device further providing the processed image data to a display device in communication with the computing device.

9. The ophthalmic surgical microscope of claim 8, wherein:
   the computing device processes the image data by overlaying the in-focus image data.

10. A method of operating an ophthalmic surgical microscope, comprising:
    controlling an optical element positioned in an optical pathway of light reflected from a surgical field towards an objective lens, the optical element comprising an optical lens, the optical element controlled by moving the optical element separately from the objective lens to generate an oscillating focal plane perpendicular to the optical pathway;
    receiving the light reflected from the surgical field at an image sensor;
    generating image data based on the light received at the image sensor, the image data being representative of a plurality of focal planes perpendicular to the optical pathway resulting from the oscillating focal plane;
    sensing an z-axis position of the optical element;
    processing the image data by selecting in-focus image data from the image data based on the sensed z-axis position of the optical element; and
    providing the processed image data to a display device.

11. The method of claim 10, wherein controlling the optical element includes:
    controlling the optical element to oscillate the oscillating focal plane at a frequency greater than the critical flicker fusion rate.

12. The method of claim 10, wherein controlling the optical element includes:
    controlling the optical element to oscillate the oscillating focal plane with a displacement in the direction along the optical pathway between approximately 200 microns and approximately 300 microns.

13. The method of claim 10, wherein controlling the optical element includes:
    providing the control signal comprising a voltage command to generate the oscillating focal plane.

14. The method of claim 10, wherein processing the image includes:
    overlaying the in-focus image data to generate the processed image data.

15. The method of claim 14, wherein selecting the in-focus image data includes:
    filtering image data with high frequency content using an electronic component.

* * * * *